United States Patent [19]

Grundei et al.

[11] Patent Number: 5,108,440
[45] Date of Patent: Apr. 28, 1992

[54] SHOULDER IMPLANT

[75] Inventors: Hans Grundei, Lübeck; Ugo de Nicola, Bad Mergentheim, both of Fed. Rep. of Germany

[73] Assignee: S & G Implants GmbH, Lubeck, Fed. Rep. of Germany

[21] Appl. No.: 560,026

[22] Filed: Jul. 25, 1990

Related U.S. Application Data

[63] Continuation of Ser. No. 349,157, May 9, 1989, abandoned.

[30] Foreign Application Priority Data

May 17, 1988 [DE] Fed. Rep. of Germany ....... 3816676

[51] Int. Cl.⁵ .............................................. A61F 2/40
[52] U.S. Cl. ...................................................... 623/19
[58] Field of Search .................... 623/18, 19, 20, 22

[56] References Cited

U.S. PATENT DOCUMENTS 4,298,993 11/1981 Kovaleva et al. .................. 623/22
4,714,473 12/1987 Bloebaum ........................... 623/20
4,828,565 5/1989 Duthoit et al. ..................... 623/18

FOREIGN PATENT DOCUMENTS 2620623 3/1989 France ................................. 623/22

Primary Examiner—David J. Isabella
Attorney, Agent, or Firm—Dvorak and Traub

[57] ABSTRACT

A shoulder implant for correcting a recurrent shoulder dislocation comprises a one-piece metal member at least part of which is open-celled in nature to simulate spongiosa of a bone. The use of the shoulder implant makes it possible to dispense with the removal of an implant of bone from the tibia or the pelvis which has been customary hitherto. Moreover, the intrinsic mechanical strength of the shoulder implant is responsible for a considerable reduction in the length of post-operative treatment. The open-celled nature of at least part of the shoulder implant in imitation of the spongiosa makes it possible for the bony matter of the scapula to anchor itself biologically in the implant, thus preventing the implant from coming loose.

4 Claims, 1 Drawing Sheet

FIG. 1
FIG. 2
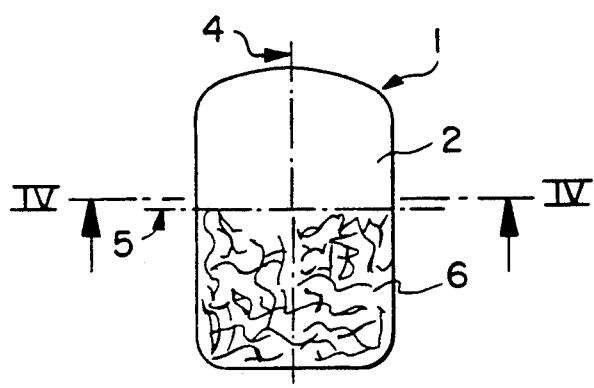
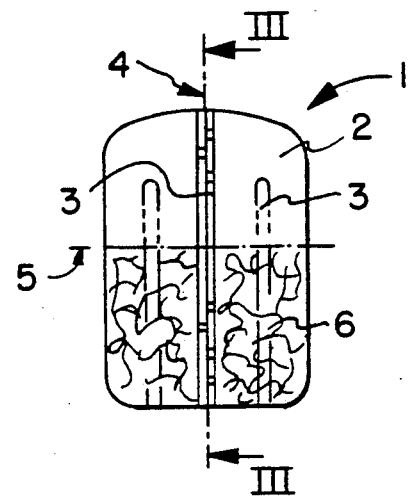
FIG. 4
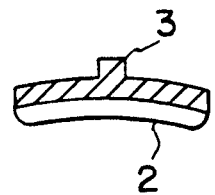
FIG. 3
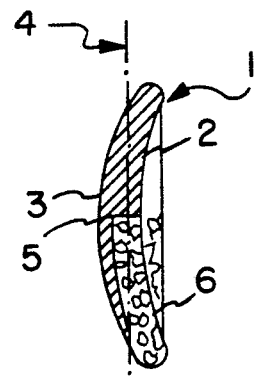
FIG. 5
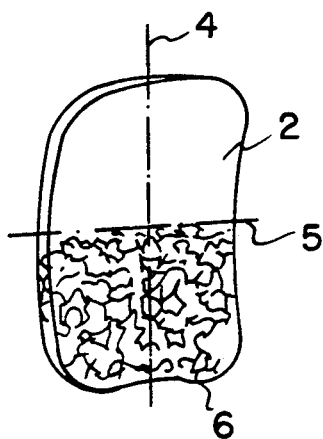

SHOULDER IMPLANT

This application is a continuation of application Ser. No. 07/349,157, filed May 9, 1989, now abandoned.

BACKGROUND OF THE INVENTION

1. Field of the Invention

The invention relates to a shoulder implant for correcting recurrent shoulder dislocation.

2. Description of the Prior Art

An indication of recurrent dislocation of the shoulder joint is the existance of an excessively narrow lower front edge to the socket of the shoulder joint. To date, surgical techniques for correcting a dislocation of this nature have envisaged taking a chip of bone from the tibia or pelvis and driving it into the scapula as a shoulder implant to widen the lower front edge of the socket of the shoulder joint. By so doing it is ensured that the gaseous shoulder implant will grow into the bone because it is material natural to the body.

However, there are felt to be disadvantages of the surgical procedures currently practised, namely that post-operative treatment requires a relatively long period and that an additional resection, which represents a stress to the body, has to be performed to remove the implant of bone from the tibia or the pelvis.

Hence, the main object of the present invention is to provide an artificial shoulder implant which simulates a chip of bone and which can be used to appreciably shorten the post-operative treatment and which removes the need for any additional resection. At the same time the aim is that,it should be possible to anchor the implant securely in the bony matter of the scapula.

SUMMARY OF THE INVENTION

To this end, the present invention consists in a shoulder implant for preventing recurrent shoulder dislocation, which is otherwise of the normal dimensions, and which comprises a one-piece member which is preferably of metal and which is at least partly of an open-celled nature to simulate the spongiosa.

By means of the invention, the bottom front edge of the socket can be widened by driving the shoulder implant into the scapula. This, of course, makes it unnecessary for an implant of bone to be removed from the tibia or the pelvis.

Moreover, the optimum mechanical strength of the proposed shoulder implant which is natural to it makes the post-operative treatment considerably shorter.

Because of the open-celled nature of at least part of the shoulder implant in imitation of the spongiosa it is possible for the bony matter of the scapula to anchor itself biologically in the implant, thus preventing the implant from coming loose.

Advantageously, approximately half of the shoulder implant comprises a section formed from metal of an open-celled nature and the other half comprises solid metal.

The one-piece configuration of the shoulder implant in itself ensures adequate strength against shear and bending forces. To increase its strength still further, it is advantageous for a stiffening rib to be provided on it dorsally. The length of this rib may be equal to the length of the implant and it may extend centrally thereto.

In view of the strength required, it is particularly advantageous for the stiffening rib to be formed in one piece with the shoulder implant.

In order to adapt it to anatomical conditions, the shoulder implant may advantageously have a concavity formed in it ventrally about its two main axes

BRIEF DESCRIPTION OF THE DRAWINGS

In order that the invention may be more readily understood an embodiment thereof will now be described, by way of example, with reference to the accompanying drawings, in which:

FIG. 1 is a plan view of the ventral surface of a shoulder implant constructed in accordance with the invention, FIG. 2 is a plan view of the dorsal surface of the shoulder implant of FIG. 1, FIG. 3 is a cross-sectional view taken on line III—III of FIG. 2, FIG. 4 is a cross-sectional view taken on line IV—IV of FIG. 1, and FIG. 5 is a perspective view angularly taken from the right side of FIG. 3.

DESCRIPTION OF THE PREFERRED EMBODIMENT

In the embodiment illustrated in the drawings, a shoulder implant is a one-piece rigid member which is of metal and of which approximately half forms a section 2 of solid metal and the other half forms an open-celled section 6 which simulates the spongiosa. In the course of a surgical operation, this section 6 is driven into the scapula. This having been done, the solid section 2 forms a widening of the bottom front edge of the socket of the shoulder joint.

After the implantation, bony tissue can grow into the open-celled material of portion 6 and ossify and the biological anchorage of the implant which arises as a result of this will prevent the implant from coming loose.

Because of its one-piece structure, the shoulder implant 1 has a certain intrinsic strength but it may still be useful to provide it with additional strength by means of a stiffening rib 3 on its dorsal side, as can be seen in FIG. 2. In the embodiment shown, the length of the stiffening rib 3 is substantially the same as the length of the shoulder implant 1. In the case of the shoulder implant 1 shown, the stiffening rib 3 extends centrally. It is however conceivable for the stiffening rib on the dorsal side of the shoulder implant 1 to be of a different size and in a different position.

For reasons of strength, the stiffening rib 3 is preferably formed in one piece with the shoulder implant 1.

As indicated in FIG. 3, the shoulder implant 1 is formed with a slight concavity about its main axis 4. In a similar fashion, a concavity is also provided around main axis 5. The concavities in the shoulder implant 1 serve to adapt to anatomical conditions in the region of the shoulder joint.

It should be appreciated that the invention is not limited to the embodiment herein described but includes all modifications and variations falling within its scope. For example, instead of being of metal, the one-piece member may be of any other suitable rigid material.

We claim:

1. A shoulder implant for correcting recurrent shoulder dislocation comprising:

an elongated metal plate divided into first and second sections, said plate having a dorsal surface and a concave ventral surface sized and configured to complement anatomical conditions in the region of the shoulder joint;

said first section being non-porous;

said second section being a porous open-celled structure which allows for anchoring to the natural bone of the scapula; and at least one rib extending outwardly along the dorsal surface across both first and second sections for stiffening said plate.

2. A shoulder implant of claim 1, wherein said dorsal surface is convex and wherein both said dorsal and ventral surfaces extend over the length of said plate.

3. A shoulder implant of claim 1, wherein the concave ventral surface is defined by curvatures about a transverse and a longitudinal axis of the plate and wherein said axes are perpendicular.

4. A shoulder implant of claim 2, wherein the concave ventral surface is defined by curvatures about a transverse and a longitudinal axis of the plate and wherein said axes are perpendicular.

* * * * *